US007772408B1

(12) United States Patent
Vennekamp et al.

(10) Patent No.: US 7,772,408 B1
(45) Date of Patent: *Aug. 10, 2010

(54) SUBSTITUTED 5-ALKOXYPSORALENS AS INHIBITORS OF POTASSIUM CHANNEL ACTIVITY IN LYMPHOCYTES AND OTHER CELLS

(75) Inventors: Julia Vennekamp, Kiel (DE); Heike Wulff, Irvine, CA (US); K. George Chandy, Irvine, CA (US); Stephan Grissmer, Blaunstein (DE); Wolfram Hansel, Kronshagen (DE)

(73) Assignee: The Regents of the University of California, Oakland, CA (US)

( * ) Notice: Subject to any disclaimer, the term of this patent is extended or adjusted under 35 U.S.C. 154(b) by 1052 days.

This patent is subject to a terminal disclaimer.

(21) Appl. No.: 10/651,618

(22) Filed: Aug. 29, 2003

Related U.S. Application Data

(60) Provisional application No. 60/406,759, filed on Aug. 29, 2002.

(51) Int. Cl.
*C07D 317/08* (2006.01)
*C07D 305/00* (2006.01)
*C07D 493/00* (2006.01)
(52) U.S. Cl. .................. 549/229; 549/263; 549/282
(58) Field of Classification Search .............. 549/282, 549/229, 263; 514/455
See application file for complete search history.

(56) References Cited

OTHER PUBLICATIONS

Vennekamp, J et al Kv1.3-blocking 5-phenylalkoxypsoralens: A new class of immunomodulators CA 141:116451 (20040.*
Caceres, A et al Furanocoumarins from the aerial parts of Dorstenia contrajerva Fitoterapia (2001), 72(4), 376-381.*
Guo, LQ et la Inhibitory effect of natural furanocoumarins on human microsomal cytochrome P450 3A activity Japanese Journal of Pharmacology (2000), 82(2), 122-129.*
Tatum, JH et al Coumarins and psoralens in grapefruit peel oil CA 91: 120313 (1979).*
Decout, JL et al Reversed-phase high-performance liquid chromatography, a tool for the study of bichromophoric systems including polymethylenic linking bridges CA 112:72955 (1990).*
Bussey, C et al Double-headed molecules based on linear or angular psoralen and <SYM97>-methylene-<SYM103>-butyrolactone: a search for non-phototoxic potential antiproliferative compounds CA 120:298501 (1994).*
Baell, JB 'Potassium channel blockers as immunosupressants' Expert Opin. Ther. Patents (2005) 15(9) 1209-1220.*
Chandy, KG et al 'K+ channels as targets for specific immunomodulation' Trends in Pharmacological Sciences 25(5) (May 2004) 280-289.*
Vennekamp, J et al 'Kv1.3-Blocking 5-Phenylalkoxypsoralens: A New class of Immunomodulators' Molecular Pharmacology 65:1364-1374, 2004.*
Griffiths, The immunological basis of psoriasis, PMID: 12795768 (2003).*
Gupta, Psoralen photochemotherapy, PMID: 3316316 (1987).*
McNeely, 5-methoxypsoralen. A review of its effects in psoriasis and vitiligo, PMID: 9806110 (1998).*
Wulff et al. Journal of Medicinal Chemistry, 1998, 41, 4542-4549.*
Wulff et al. Journal of Medicinal Chemistry, 1998, 41, 4542-4549.*
Musajo et al. STN Accession No. 1959:34784 Document No. 53:34784 Abstract of Farmaco, Edizione Scientifica (1958), 13, 355-62.*
Michael D. Cahalan et al., "Ion channels in the immune system as target for immunosuppression", Pharmaceutical Biotechnology, pp. 749-756.
Gloria C. Koo et al., "Correolide and Derivatives Are Novel Immunosuppressants Blocking the Lymphocyte Kv1.3 Potassium Channels", Cellular Immunology, No. 197 (1999), pp. 99-107.
Gloria C. Koo et al., "Blockade of the Voltage-Gated Potassium Channel Kv1.3 Inhibits Immune Responses in Vivo", The Journal of Immunology, 0022-1767 (1997) pp. 5120-5128.
Christine Beeton et al., "A novel Fluorescent Toxin to Detect and Investigate Kv1.3 Channel Up-regulation in Chronically Activated T Lymphocytes", The Journal of Biological Chemistry, vol. 278, No. 11, (Mar. 14, 2003), pp. 9928-9937.
Heike Wulff et al., "The voltage-gated Kv1.3 $K^+$ channel in effector memory T cell as new target for MS", The Journal of Clinical Investigation, vol. 111, No. 11, (Jun. 2003), pp. 1703-1713.
Christine Beeton et al., "Selective blockade of T lymphocyte $K^+$ channels ameliorates experimental autoimmune encephalomyelitis, a model for multiple sclerosis", PNAS, vol. 98, No. 24 (Nov. 20, 2001), pp. 13942-13947.
Heike Wulff et al., "Alkoxypsoralens, Novel Nonpeptide Blockers of Shaker-Type $K^+$ Channels: Synthesis and Photoreactivity", Journal of Medical Chemistry, vol. 41, No. 23 (1998), pp. 4542-4549.
T. Düring et al., "Effects of Three Alkoxypsoralens on Voltage Gated Ion Channels in Ranvier Nodes", Gen. Physiol. Biophys, vol. 19 (2000), pp. 345-364.
K.H. Bohuslavizki et al., "Mode of Action of Psoralens, Benzofurans, Acridinons, and Coumarins on the Ionic Currents in Intact Myelinated Nerve Fibers and its Significance in Demyelinating Disease", Gen. Physiol. Biophys, vol. 13 (1994), pp. 309-328.

(Continued)

*Primary Examiner*—D. Margaret Seaman
*Assistant Examiner*—Nizal S Chandrakumar
(74) *Attorney, Agent, or Firm*—Robert D. Buyan; Stout, Uxa, Buyan & Mullins (57) ABSTRACT

Compositions of matter comprising 5-phenylalkoxypsoralen compounds and their method of synthesis and use. The compounds are useable to treat diseases or disorders in human or veterinary patients, including autoimmune diseases such as multiple sclerosis. The compounds inhibit potassium channels, including the Kv1.3 channel and at least some of the therapeutic effects of such compounds may be due at least in part to potassium channel inhibition.

14 Claims, 2 Drawing Sheets

OTHER PUBLICATIONS

Karl H. Bohuslavizki et al., "*Reduction of MS-related scotomata by a new class of potassium channel blockers from Ruta graveolens*", Neuro-ophthalmology, vol. 13, No. 4 (1993), pp. 191-198.

Ulf Strauss et al., "*K+ channel-blocking alkoxypsoralens inhibit the immune response of encephalitogenic T line cells and lymphocytes from Lewis rats challenged for experimental autoimmune encephalomyelitis*", Immunopharmacology, vol. 48 (2000), pp. 51-63.

* cited by examiner

SUBSTITUTED 5-ALKOXYPSORALENS AS INHIBITORS OF POTASSIUM CHANNEL ACTIVITY IN LYMPHOCYTES AND OTHER CELLS

RELATED APPLICATIONS

This application claims the benefit of U.S. Provisional Application Ser. No. 60/406,759 filed Aug. 29, 2002. The entire disclosure of this provisional application is expressly incorporated herein by reference

BACKGROUND OF THE INVENTION

In the early 1990s, there appeared anecdotal reports suggesting that the symptoms of multiple sclerosis (MS) were alleviated by drinking tea made from the plant Ruta graveolens. Various laboratory studies were then undertaken in efforts to identify the pharmacologically active component(s) of Ruta graveolens. It was determined that extracts from Ruta graveolens could block delayed-rectifier potassium currents in nodes of Ranvier (Bohuslavizki K. H. et al., 1994, *Gen. Physiol. Biophys.* 13: 309). On this basis, it was postulated that certain component(s) of Ruta graveolens blocked potassium currents in either neurons that had become demyelinated due to MS or in myelin-reactive lymphocytes. 5-Methoxypsoralen (5-MOP), a compound that has been clinically used in the treatment of psoriasis was identified as a component of Ruta graveolens that blocked Kv1.2 channels in neurons and Kv1.3 channels in T cells (Wulff et al., 1998, *J. Med. Chem.* 41: 4542). Subsequent single case studies indicated that the administration of 5-MOP alleviate the symptoms of MS in several patients with MS (Bohuslavizki K. H. et al., 1993, *Neuroopthalmol.* 13: 191). However, 5-MOP blocks potassium channels with a very low affinity (Kd=100 μM). Thus, there remained a need in the art for the synthesis and/or identification of new psoralen compounds that would inhibit potassium channels much more potently and thus provide therapeutic efficacy against MS and other autoimmune disorders.

Kv1.3 Channel in T Cells.

The predominant voltage-gated channel in human T-lymphocytes is encoded by Kv1.3, a Shaker-related gene. Kv1.3 has been characterized extensively at the molecular and physiological level and plays a vital role in controlling T-lymphocyte proliferation, mainly by maintaining the resting membrane potential of resting T-lymphocytes. Recently, encephalitogenic and arthritogenic rat T cells that were chronically activated with myelin antigens, were found to express a unique channel phenotype (high Kv1.3 channels and low IKCa1 channels), distinct from that seen in quiescent and acutely activated T cells (Beeton et al., 2001, *Proc. Natl. Acad. Sci. USA* 98:13942). In a subsequent study, we have confirmed this finding in myelin antigen specific T cells from patients with MS. Contrary to myelin-reactive T cells from healthy controls and to mitogen or control antigen activated T cells from MS patients, myelin reactive T cells from MS patients predominantly expressed surface markers of terminally differentiated effector memory T cells (CCR7$^-$CD45RA$^-$) and exhibited the Kv1.3$^{high}$ IKCa1$^{low}$ phenotype (Wulff et al., 2003, *J. Clin. Invest.* 111:1703). In the same study we could show that this special K$^+$ channel phenotype made the proliferation of effector memory T cells highly sensitive to inhibition by Kv1.3 blockers. Naïve and central memory T cells were only affected at 10-fold higher concentrations of Kv1.3 blockers and could escape Kv1.3 inhibition during subsequent stimulation through the up-regulation of the calcium-activated potassium channel IKCa1. It would be thus possible to target the disease-inducing effector memory T cell population without affecting the normal immune response. In a proof of this concept the Kv1.3-blocking peptide ShK has been recently shown to prevent and treat experimental autoimmune encephalomyelitis in Lewis rats, an animal model for MS (Beeton et al., 2001, *Proc. Natl. Acad. Sci. USA* 98:13942).

Kv1.3 and IKCa1 Expression and Functional Roles in Human Naïve and Memory T-Cells Human T-cells are divided into three subsets, naïve, central memory T ($T_{CM}$) and effector memory T ($T_{EM}$) cells, based on the expression of the chemokine receptor CCR7 and the phosphatase CD45RA. Naïve (CCR7$^+$CD45RA$^+$) and $T_{CM}$ (CCR7$^+$CD45RA$^-$) cells migrate to the lymph node using CCR7 as an entry code, before migrating to sites of inflammation. In contrast, $T_{EM}$ cells have the ability to home directly to sites of inflammation, where they can secrete high amounts of interferon (IFN)-γ and tumor necrosis factor (TNF)-α and exhibit immediate effector function. The expression patterns of Kv1.3 and IKCa1 change dramatically as naïve cells become memory cells. At rest, CD4$^+$ and CD8$^+$T-cells of all three subsets exhibit ~200 to 400 Kv1.3 channels, and 0 to 30 IKCa1 channels (Wulff et al., 2003, *J. Clin. Invest.* 111:1703). Activation has diametrically opposite effects on channel expression; as naïve and $T_{CM}$ cells move from resting to proliferating blast cells, they transcriptionally up-regulate IKCa1 to ~500 channels per cell. In contrast, activation of $T_{EM}$ cells enhances Kv1.3 expression without any change in IKCa1 levels (Wulff et al., 2003, *J. Clin. Invest.* 111:1703). Functional Kv1.3 expression increases dramatically within 15 h of activation to a level of 1500 Kv1.3 channels/cell, remains elevated for the following 48 to 72 h, and then returns to baseline over the next five days (Beeton et al., 2003, *J. Biol. Chem.* 278:9928)

The subset-specific channel expression has important functional consequences, since Kv1.3 and IKCa1 regulate Ca$^{2+}$ entry into T-cells through Ca$^{2+}$-release-activated Ca$^{2+}$ (CRAC) channels that exhibit 'upside-down' voltage-dependence compared with voltage-gated Ca$^{2+}$ channels. A negative membrane potential drives Ca$^{2+}$ entry through CRAC channels. The electrochemical gradient supporting Ca$^{2+}$ entry is initially large, resulting in significant Ca$^{2+}$ influx. However, Ca$^{2+}$ entry results in depolarization of the plasma membrane, limiting further influx. To maintain Ca$^{2+}$ entry over the time scale required for gene transcription, a balancing cation efflux is necessary; this is provided by the efflux of K$^+$ ions through Kv1.3 and/or IKCa1 channels, which supply the electrochemical driving force for Ca$^{2+}$ entry via membrane hyperpolarization.

Depolarization resulting from Kv1.3 and IKCa1 blockade is inhibitory for Ca$^{2+}$ influx, signaling and lymphocyte activation. As Kv1.3 channels predominate in resting T-cells of the three subsets, the Kv1.3 blocker ShK, but not the IKCa1 blocker TRAM-34, suppress antigen or mitogen-driven activation. However, ShK is 10-fold more effective on $T_{EM}$ cells than on naïve and $T_{CM}$ cells (IC$_{50}$ values of 400 pM and 4 nM, respectively), due to the fact that the latter cells rapidly up-regulate IKCa1 after stimulation and become less sensitive to Kv1.3 inhibitors (Wulff et al., 2003, *J. Clin. Invest.* 111: 1703). Once IKCa1 is up-regulated in naïve and $T_{CM}$ cells, the reactivation of these cells is sensitive to IKCa1 but not Kv1.3 blockade. Naïve and $T_{CM}$ cells can up-regulate IKCa1 following mitogen or antigen stimulation, even if their initial activation is suppressed by Kv1.3 blockade; and can consequently escape further inhibition by Kv1.3 inhibitors (Wulff et al., 2003, *J. Clin. Invest.* 111:1703). Early in vivo studies support these in vitro findings. The Kv1.3 blockers MgTX (Koo et al., 1997, *J. Immunol.* 158:1520) and correolide (Koo et al., 1999, *Cell Immunol.* 197:99) effectively suppress the primary delayed-type hypersensitivity (DTH) response in mini-pigs, but are much less effective in suppressing the secondary DTH response, presumably due to the fact that the activated naïve or $T_{CM}$ cells involved have up-regulated IKCa1 expression. In contrast, $T_{EM}$ cells exclusively up-regulate Kv1.3 channels, and are persistently suppressed by Kv1.3 inhibitors.

SUMMARY OF THE INVENTION

The present invention provides 5-phenylalkoxypsoralens, a new class of small-molecules that block the Kv1.3 channel in the low nanomolar range and preferentially suppress the proliferation of effector memory T cells and affect naïve and central memory T cells only at much higher concentrations. Given the known in vitro and in vivo effects of peptide and non-peptide inhibitors of the Kv1.3 channel, the present invention further comprises the therapeutic and/or diagnostic use of these 5-phenylalkoxypsoralens for any diagnosis or treatment that results from or is facilitated by blocking or inhibiting of the Kv1.3 channel, including but not limited to the use of 5-phenylalkoxypsoralens as immunosuppressants and/or for the treatment of multiple sclerosis, rheumatoid arthritis, graft rejection and/or any autoimmune disorders.

Current immunosuppressive therapy with cyclosporin A is limited by severe side effects such as liver and renal damage. Selective blockers of Kv1.3 including the herein-disclosed 5-phenylalkoxypsoralens might possibly be free of these side-effects and could thus, either as a monotherapy or in combination with cyclosporin A, considerably improve the treatment of heart, kidney and liver transplant rejection (Cahalan M D and Chandy K G, 1997, Curr. Opin. Biotechnol. 8:749).

For Multiple Sclerosis in particular, the current therapy with interferon-beta and copaxone only benefits about 60% of patients. The appearance of neutralizing antibodies in around 40% of patients treated with interferon-beta makes interferon-beta treatment less effective over time in the responsive patients. There clearly is an urgent need for new MS drugs, such as the 5-phenylalkoxypsoralens disclosed herein.

A first broad aspect of the invention is directed to compositions of matter comprising and consisting of the aforementioned 5-phenylalkoxypsoralens, which are represented by Formula I below:

Formula I 5-alkoxypsoralens where:

R1 is selected from aryl, heterocyclyl or cycloalkyl, optionally substituted with one or more substituents selected from alkyl, alkoxy, amino and its alkyl derivatives, acy- lamino, carboxyl and its alkyl ester, cyano, halo, hydroxy, nitro and sulfonamido groups; and X is selected from a saturated or unsaturated, chiral or achiral, cyclic or acyclic hydrocarbyl group with from 2 to 10 carbon atoms, optionally substituted with alkyl, cycloalkyl and aryl group.

In the most preferred compounds of this invention, R1 is aryl and cycloalkyl; X is a hydrocarbyl group with from 2 to 5 carbon atoms.

A second broad aspect of the invention is directed to preparations for administration to human or veterinary patients, said preparations comprising a 5-phenylalkoxypsoralens as described herein or a pharmaceutically acceptable salt thereof, and possibly including pharmaceutically acceptable carriers, excipients and other ingredients commonly used in pharmaceutical preparations for oral, parenteral, trans-mucosal, trans-dermal, topical and/or other possible route(s) of administration.

Another broad aspect of the invention is directed to a method for treating, diagnosing or preventing a disease or disorder in human or veterinary patient, the method comprising the step of administering to the patient a diagnostically, therapeutically or preventively effective amount of a 5-phenylalkoxypsoralen as described herein.

One preferred embodiment of the above method is particularly applicable to diseases that are treatable, diagnosable or preventable by blocking or inhibiting the Kv1.3 channel. In this embodiment, the method further comprises administering to the patient a 5-phenylalkoxypsoralen in an amount that is effective to block or inhibit Kv1.3 channels.

In a more specific embodiment, the disease being treated is multiple sclerosis or any other autoimmune disease or disorder.

Further aspects and advantages of the invention will become apparent to persons of skill in the art upon reading and understanding of the detailed descriptions of the preferred embodiments set forth herebelow.

DETAILED DESCRIPTION AND EXAMPLES

A series of substituted 5-alkoxypsoralens, that block the Kv1.3 channel and suppress the proliferation of effector memory T cells in the low nanomolar range, have been synthesized. These substituted 5-alkoxypsoralens are novel and significantly more potent in blocking Kv1.3 than any other known small molecule Kv1.3 blockers. Given the known in vitro and in vivo effects of peptide and non-peptide inhibitors of the Kv1.3 channel, it is easy to envision the therapeutic potential of the substituted 5-alkoxypsoralens as immunosuppressants for the treatment of multiple sclerosis and other autoimmune disorders.

These novel alkoxypsoralens are represented by Formula I below:

Formula I

5-alkoxypsoralens

5-Benzyloxysporalen (CAS registry number 109 559-62-8) is a known compound with no biological activity reported in Chemical Abstract System. The other compounds represented by Formula I are new.

The compounds were synthesized according to the following scheme:

5-Phenylalkoxy- and 5-Cyclohexylalkoxypsoralens-Synthesis and Physical Data

Synthetic Route

Example 1

Synthesis of 5-hydroxypsoralen (bergaptol)

A solution of iodine (1.0 g, 4 mmol) and magnesium (0.2 g, 8 mmol) was stirred in anhydrous ether (30 ml) under reflux until colourless to prepare magnesium iodide. Bergapten (1.0 g, 4.5 mmol) was suspended in anhydrous ether and added to the solution. After heating the mixture to reflux for 45 min, the solvent was removed under reduced pressure. The residue was dried at 120° C. for 30 min, kept at 160-165° C. for 90 min, and decomposed with 25% sulfuric acid. The crude product was filtered, washed with a solution of thiosulfate, dried, and used for the synthesis of the 5-phenylalkoxy- and 5-cyclohexylalkoxypsoralens without further purification.

General Method for the Synthesis of the 5-phenylalkoxy- and 5-cyclohexylalkoxypsoralens

To a solution of bergaptol (300 mg, 1.5 mmol) in anhydrous acetone (15 ml) were added potassium carbonate (0.6 g), a small amount of potassium iodide, and an excess of the respective alkylating agent. The mixture was stirred under nitrogen and heated to reflux. After the required reaction time, the mixture was poured into water and acidified with HCl. The precipitate was collected by vacuum filtration, dissolved in $CH_2Cl_2$, and extracted with 2% NaOH. The solvent was removed under reduced pressure and the crude product recrystallized from $EthOH/H_2O$.

Spectroscopy

IR-Spectroscopy: s=strong, m=middle $^1$H-NMR-Spectroscopy: s=singlet, d=doublet, dd=doublet of doublet, ddd=doublet of doublet of doublet, t=triplet, dt=doublet of triplet, quint=quintet, sext=sextet, m=multiplet, br=broad signal, J=coupling constant; internal standard: tetramethylsilane (TMS)

To assign the NMR signals, the structures are numbered as follows:

Example 2

5-Benzyloxypsoralen (5-BOP)

4-Benzyloxy-7H-furo[3,2-g][1]benzopyran-7-one 200 mg (1 mmol) of bergaptol and 4.3 g (25 mmol) of benzylbromide were reacted according to the general method. The reaction time was 24 h. The product was recrystallized from MeOH/H$_2$O.

Yield: 240 mg (82%)

Melting point: 136° C., Lit.: 142° C. (Caporale G. und Antonella G.; Farmaco, 13 (1958) 363-367)

IR (KBr, [cm$^{-1}$]): 1700 ($v_{C=O}$); 1610 ($v_{C=C}$)

$^1$H-NMR (300 MHz, CDCl$_3$, δ [ppm]): 5.44 (s, 2H, 5-OCH$_2$C$_6$H$_5$); 6.22 (d, 1H, $^3$J=9.8 Hz, 3-H); 6.93 (d, 1H, $^3$J=2.3 Hz, 4'-H); 7.17 (s, 1H, 8-H); 7.38-7.41 (m, 5H, 5-OCH$_2$C$_6$H$_5$); 7.58 (d, 1H, $^3$J=2.3 Hz, 5'-H); 8.07 (d, 1H, $^3$J=9.8 Hz, 4-H)

C$_{18}$H$_{12}$O$_4$ (292.29)

Example 3

5-(2-Phenylethoxy)psoralen (J 09)

4-(2-Phenylethoxy)-7H-furo[3,2-g][1]benzopyran-7-one 150 mg (0.7 mmol) of bergaptol, 2 ml (14.8 mmol) of 2-phenylethylbromide, and 0.2 g K$_2$CO$_3$ in a solution of 10 ml Acetone were reacted according to the general method. The reaction time was 5 h. The product was recrystallized from MeOH/H$_2$O.

Yield: 90 mg (40%)

Melting point: 154.5° C.

IR (KBr, [cm$^{-1}$]): 1720 (s, $v_{C=O}$); 1624 and 1604 (s, $v_{C=C}$); 749 (m, δ$_{CH}$)

$^1$H-NMR (300 MHz, CDCl$_3$, δ [ppm]): 3.18 (t, 2H, $^3$J=6.7 Hz, 5-OCH$_2$CH$_2$C$_6$H$_5$); 4.65 (t, 2H, $^3$J=6.7 Hz, 5-OCH$_2$CH$_2$C$_6$H$_5$); 6.21 (d, 1H, $^3$J=9.8 Hz, 3-H); 6.84 (dd, 1H, $^3$J=2.4 Hz, $^5$J=0.9 Hz, 4'-H); 7.14 (s, br, 1H, 8-H); 7.28-7.38 (m, 5H, 5-O(CH$_2$)$_2$C$_6$H$_5$); 7.56 (d, 1H, $^3$J=2.4 Hz, 5'-H); 7.94 (d, 1H, $^3$J=9.8 Hz, 4-H)

$^{13}$C-NMR (75.5 MHz, CDCl$_3$, δ [ppm]): 36.50 (5-OCH$_2$CH$_2$C$_6$H$_5$); 73.62 (5-OCH$_2$CH$_2$C$_6$H$_5$); 94.28 (8-C); 104.89 (4'-C); 107.12 (4a-C); 112.68 (3-C); 113.76 (6-C); 126.90 (4''-C); 128.74 and 129.00 (2''-C, 3''-C, 5''-C, 6''-C); 137.54 (1''-C); 139.24 (4-C); 144.93 (5'-C); 148.69 (5-C); 152.66 (8a-C); 158.16 (7-C); 161.18 (2-C)

MS (70 eV, m/z, I [% B]): 306 (6, M$^+$); 106 (9); 105 (100, [C$_8$H$_9$]$^+$); 103 (7); 89 (3); 79 (16); 78 (2); 77 (13, [C$_6$H$_5$]$^+$); 63 (2); 51 (6, [C$_4$H$_3$]$^+$)

| C$_{19}$H$_{14}$O$_4$ (306.32): | calculated: | C 74.50% | H 4.61% | O 20.89% |
|---|---|---|---|---|
| | found: | C 74.43% | H 4.67% | O 20.90% |

Example 4

5-(3-Phenylpropoxy)psoralen (J 15, Psora-3)

4-(3-Phenylpropoxy)-7H-furo[3,2-g][1]benzopyran-7-one 0.3 ml (2 mmol) 3-phenylpropylbromide were reacted according to the general method. The reaction time was 8 h.

Yield: 120 mg (25%)

Melting point: 109° C.

IR (KBr, [cm$^{-1}$]): 1726 (s, $v_{C=O}$); 1620 and 1607 (s, $v_{C=C}$)

$^1$H-NMR (300 MHz, CDCl$_3$, δ [ppm]): 2.22 (quint, 2H, $^3$J≈6.9 Hz, 5-OCH$_2$CH$_2$CH$_2$C$_6$H$_5$); 2.88 (t, 2H, $^3$J=7.5 Hz, 5-O(CH$_2$)$_2$CH$_2$C$_6$H$_5$); 4.46 (t, 2H, $^3$J=6.3 Hz, 5-OCH$_2$(CH$_2$)$_2$C$_6$H$_5$); 6.27 (d, 1H, $^3$J=9.8 Hz, 3-H); 6.85 (dd, 1H, $^3$J=2.2 Hz, $^5$J=0.8 Hz, 4'-H); 7.13 (s, 1H, 8-H); 7.21-7.34 (m, 5H, 5-O(CH$_2$)$_3$C$_6$H$_5$); 7.55 (d, 1H, $^3$J=2.4 Hz, 5'-H); 8.10 (d, 1H, $^3$J=9.8 Hz, 4-H)

$^{13}$C-NMR (75.5 MHz, CDCl$_3$, δ [ppm]): 31.45 and 32.17 (5-OCH$_2$(CH$_2$)$_2$C$_6$H$_5$); 71.91 (5-OCH$_2$(CH$_2$)$_2$C$_6$H$_5$); 93.90 (8-C); 105.10 (4'-C); 106.73 (4a-C); 112.59 (3-C); 113.21 (6-C); 126.25 (4''-C); 128.45 and 128.62 (2''-C, 3''-C, 5''-C, 6''-C); 139.29 (4-C); 140.86 (4''-C); 144.77 (5'-C); 148.91 (5-C); 152.72 (8a-C); 158.28 (7-C); 161.23 (2-C)

MS (70 eV, m/z, I [% B]): 320 (16, M$^+$); 202 (25, [M-C$_9$H$_{10}$]$^+$); 174 (7, [202-CO]$^+$); 119 (10, [C$_9$H$_{11}$]$^+$); 92 (8); 91 (100, [C$_7$H$_7$]$^+$); 89 (5); 65 (8, [C$_5$H$_5$]$^+$); 51 (7, [C$_4$H$_3$]$^+$); 41 (13)

| C$_{20}$H$_{16}$O$_4$ (320.34): | calculated: | C 74.99% | H 5.03% | O 19.98% |
|---|---|---|---|---|
| | found: | C 74.20% | H 5.14% | O 19.66% |

Example 5

5-(4-Phenylbutoxy)psoralen (J 19, Psora-4)

4-(4-Phenylbutoxy)-7H-furo[3,2-g][1]benzopyran-7-one 0.5 ml (3 mmol) of 4-phenylbutylchloride were reacted according to the general method. The reaction time was 31 h.

Yield: 109 mg (22%)

Melting point: 98° C.

IR (KBr, [cm$^{-1}$]): 1727 (s, $\nu_{C=O}$); 1622 and 1604 (s, $\nu_{C=C}$)

$^1$H-NMR (300 MHz, CDCl$_3$, δ [ppm]): 1.86-1.91 (m, 4H, 5-OCH$_2$(CH$_2$)$_2$CH$_2$C$_6$H$_5$); 2.73 (t, 2H, $^3$J=7.2 Hz, 5-O(CH$_2$)$_3$ CH$_2$C$_6$H$_5$); 4.44 (t, 2H, $^3$J=6.0 Hz, 5-OCH$_2$(CH$_2$)$_3$C$_6$H$_5$); 6.27 (d, 1H, $^3$J=9.8 Hz, 3-H); 6.89 (dd, 1H, $^3$J=2.4 Hz, $^5$J=1.0 Hz, 4'-H); 7.13 (dd, 1H, $^5$J=0.9 Hz, $^5$J=0.7 Hz, 8-H); 7.18-7.23 and 7.27-7.33 (2x m, 3H and 2H, 5-O(CH$_2$)$_4$C$_6$H$_5$); 7.57 (d, 1H, $^3$J=2.4 Hz, 5'-H); 8.12 (dd, 1H, $^3$J=9.8 Hz, $^5$J=0.7 Hz, 4-H)

$^{13}$C-NMR (75.5 MHz, CDCl$_3$, δ [ppm]): 27.70 and 29.56 (5-OCH$_2$(CH$_2$)$_2$CH$_2$C$_6$H$_5$); 35.52 (5-O(CH$_2$)$_3$CH$_2$C$_6$H$_5$); 72.82 (5-OCH$_2$(CH$_2$)$_3$C$_6$H$_5$); 93.95 (8-C); 105.10 (4'-C); 106.83 (4a-C); 112.62 (3-C); 113.35 (6-C); 126.03 (4"-C), 128.41 and 128.46 (2"-C, 3"-C, 5"-C, 6"-C); 139.31 (4-C); 141.78 (1"-C); 144.78 (5'-C); 149.01 (5-C); 152.74 (8a-C); 158.28 (7-C); 161.25 (2-C)

MS (70 eV, m/z I [% B]): 334 (5, M$^+$); 203 (5); 202 (33, [M-C$_{10}$H$_{12}$]$^+$); 174 (6, [202-CO]$^+$); 133 (7, [C$_{10}$H$_{13}$]$^+$); 92 (8); 91 (100, [C$_7$H$_7$]$^+$); 65 (7, [C$_5$H$_5$]$^+$); 51 (6, [C$_4$H$_3$]$^+$); 44 (6)

| C$_{21}$H$_{18}$O$_4$ (334.37): | calculated: | C 75.43% | H 5.43% | O 19.14% |
|---|---|---|---|---|
| | found: | C 75.34% | H 5.41% | O 19.25% |

Example 6

5-(5-Phenylpentoxy)psoralen (J 22)

4-(5-Phenylpentoxy)-7H-furo[3,2-g][1]benzopyran-7-one 0.7 ml (3.9 mmol) of 5-phenylpentylchloride were reacted according to the general method. The reaction time was 27 h.

Yield: 125 mg (24%)

Melting point: 94.5° C.

IR (KBr, [cm$^{-1}$]): 1720 (s, $\nu_{C=O}$); 1622 and 1605 (s, $\nu_{C=C}$), 748 (s, $\delta_{CH}$)

$^1$H-NMR (300 MHz, CDCl$_3$, δ [ppm]): 1.53-1.59, 1.69-1.77 und 1.85-1.95 (3x m, 3x 2H, 5-OCH$_2$(CH$_2$)$_3$CH$_2$C$_6$H$_5$); 2.67 (t, 2H, $^3$J=7.5 Hz, 5-O(CH$_2$)$_4$CH$_2$C$_6$H$_5$); 4.43 (t, 2H, $^3$J=6.4 Hz, 5-OCH$_2$(CH$_2$)$_4$C$_6$H$_5$); 6.25 (d, 1H, $^3$J=9.8 Hz, 3-H); 6.91 (dd, 1H, $^3$J=2.4 Hz, $^5$J=1.0 Hz, 4'-H); 7.12 (t, 1H, $^5$J=0.8 Hz, 8-H); 7.17-7.21 and 7.25-7.31 (2x m, 3H und 2H, 5-O(CH$_2$)$_4$C$_6$H$_5$); 7.57 (d, 1H, $^3$J=2.4 Hz, 5'-H); 8.08 (dd, 1H, $^3$J=9.8 Hz, $^5$J=0.6 Hz, 4-H)

$^{13}$C-NMR (75.5 MHz, CDCl$_3$, δ [ppm]): 25.50 (5-O(CH$_2$)$_2$CH$_2$(CH$_2$)$_2$C$_6$H$_5$); 29.88 und 31.01 (5-OCH$_2$CH$_2$CH$_2$CH$_2$CH$_2$C$_6$H$_5$); 35.72 (5-O(CH$_2$)$_4$CH$_2$C$_6$H$_5$); 72.82 (5-OCH$_2$(CH$_2$)$_4$C$_6$H$_5$); 93.86 (8-C); 105.14 (4'-C); 106.79 (4a-C); 112.56 (3-C); 113.27 (6-C); 125.84 (4"-C); 128.36 and 128.40 (2"-C, 3"-C, 5"-C, 6"-C); 139.32 (4-C); 142.15 (1"-C); 144.75 (5'-C); 149.03 (5-C); 152.73 (8a-C); 158.28 (7-C); 161.26 (2-C)

MS (70 eV, m/z I [(% B]): 348 (10, M$^+$); 203 (7); 202 (49, [M-C$_{11}$H$_{14}$]$^+$); 174 (8, [202-CO]$^+$); 105 (8); 91 (100, [C$_7$H$_7$]$^+$); 65 (7, [C$_5$H$_5$]$^+$); 51 (6, [C$_4$H$_3$]$^+$); 49 (5); 41 (9)

| C$_{22}$H$_{20}$O$_4$ (348.40): | calculated: | C 75.84% | H 5.79% | O 18.37% |
|---|---|---|---|---|
| | found: | C 75.93% | H 5.75% | O 18.32% |

Example 7

5-Biphenylmethoxypsoralen (J 20)

4-Diphenylmethoxy-7H-furo[3,2-g][1]benzopyran-7-one 200 mg (1 mmol) of bergaptol, 250 mg (1.2 mmol) of biphenylmethylchloride, and 0.4 g $K_2CO_3$ in 10 ml of acetone were reacted according to the general method. The reaction time was 6 h. The product was recrystallized from acetone.

Yield: 120 mg (33%)

Melting point: 187° C.

IR (KBr, [cm$^{-1}$]): 1732 (s, $v_{C=O}$); 1628 (m, $v_{C=C}$); 749 (m, $\delta_{CH}$)

$^1$H-NMR (300 MHz, CDCl$_3$, $\delta$ [ppm]): 5.49 (s, 2H, 5-OC$\underline{H}_2$C$_6$H$_4$C$_6$H$_5$); 6.24 (d, 1H, $^3$J=9.8 Hz, 3-H); 6.97 (dd, 1H, $^3$J=2.4 Hz, $^5$J=1.0 Hz, 4'-H); 7.19 (s, br, 1H, 8-H); 7.34-7.66 (m, 10H, 5-OCH$_2$C$_6$$\underline{H}_4$C$_6$$\underline{H}_5$ and 5'-H); 8.11 (dd, 1H, $^3$J=9.8 Hz, $^5$J=0.6 Hz, 4-H)

$^{13}$C-NMR (75.5 MHz, CDCl$_3$, $\delta$ [ppm]): 74.86 (5-$\underline{C}$H$_2$C$_6$H$_4$C$_6$H$_5$); 94.64 (8-C); 104.94 (4'-C); 107.49 (4a-C); 112.92 (3-C); 114.14 (6-C); 127.13, 127.57, 128.30 and 128.89 (2"-C, 3"-C, 6"-C, 7"-C, 9"-C, 10"-C, 11"-C, 12"-C); 127.65 (8"-C), 135.01 (1"-C); 139.30 (4-C); 140.42 and 141.72 (4"-C, 5"-C); 145.15 (5'-C); 148.67 (5-C); 152.68 (8a-C); 158.18 (7-C); 161.12 (2-C)

MS (70 eV, m/z, I [% B]): 368 (0.2, M$^+$); 168 (15); 167 (100, [C$_{13}$H$_{11}$]$^+$); 166 (5); 165 (17); 152 (11); 145 (4); 115 (4); 89 (9); 63 (8); 51 (11, [C$_4$H$_3$]$^+$)

| $C_{24}H_{16}O_4$ (368.39): | calculated: | C 78.25% | H 4.38% | O 17.37% |
|---|---|---|---|---|
| | found: | C 78.28% | H 4.34% | O 17.38% |

Example 8

5-Diphenylmethoxypsoralen (J 17)

4-Diphenylmethoxy-7H-furo[3,2-g][1]benzopyran-7-on 200 mg (1 mmol) of bergaptol, 0.4 g (1.6 mmol) of diphenylmethylbromide, and 0.4 g $K_2CO_3$ in 15 ml of acetone were reacted according to the general method at room temperature. The reaction time was 45 h. The product was recrystallized from acetone/$H_2O$.

Yield: 132 mg (36%)

Melting point: 173° C.

IR (KBr, [cm$^{-1}$]): 1726 (s, $v_{C=O}$), 1618 and 1604 (s, $v_{C=C}$), 745 (s, $\delta_{CH}$)

$^1$H-NMR (300 MHz, CDCl$_3$, $\delta$ [ppm]): 6.29 (d, 1H, $^3$J=9.8 Hz, 3-H); 6.43 (s, 1H, 5-OC$\underline{H}$(C$_6$H$_5$)$_2$); 6.57 (dd, 1H, $^3$J=2.4 Hz, $^5$J=1.0 Hz, 4'-H); 7.18 (t, 1H, $^5$J=0.8 Hz, 8-H); 7.30-7.41 (m, 10H, 5-OCH(C$_6$$\underline{H}_5$)$_2$); 7.49 (d, 1H, $^3$J=2.4 Hz, 5'-H); 7.88 (dd, 1H, $^3$J=9.8 Hz, $^5$J=0.6 Hz, 4-H)

$^{13}$C-NMR (75.5 MHz, CDCl$_3$, $\delta$ [ppm]): 87.15 (5-O$\underline{C}$H(C$_6$H$_5$)$_2$); 95.24 (8-C); 104.65 (4'-C); 108.63 (4a-C); 113.01 (3-C); 115.64 (6-C); 127.02 and 128.76 (2"-C, 3"-C, 5"-C, 6"-C); 128.40 (4"-C); 139.37 (4-C); 140.35 (1"-C); 145.24 (5'-C); 148.10 (5-C); 152.49 (8a-C); 157.86 (7-C); 161.05 (2-C)

MS (70 eV, m/z, I [% B]): 368 (1, M$^+$); 202 (100, [M-C$_{13}$H$_{10}$]$^+$); 174 (71, [202-CO]$^+$); 167 (20, [C$_{13}$K$_{11}$]$^+$); 118 (38, [174-2CO]$^+$); 90 (40); 89 (45); 51 (50, [C$_4$H$_3$]$^+$); 50 (35); 49 (38); 44 (46)

| $C_{24}H_{16}O_4$ (368.39): | calculated: | C 78.25% | H 4.38% | O 17.37% |
|---|---|---|---|---|
| | found: | C 78.17% | H 4.38% | O 17.45% |

Example 9

R,S-5-(2-Phenylpropoxy)psoralen (J 12)

R,S-4-(2-Phenylpropoxy)-7H-furo[3,2-g][1]benzopyran-7-on 0.6 ml (3.8 mmol) of β-bromcumene were reacted according to the general method. The reaction time was 28 h.

Yield: 97 mg (20%)

Melting point: 141.5° C.

IR (KBr, [cm$^{-1}$]): 1717 (s, $v_{C=O}$); 1624 and 1605 (s, $v_{C=C}$); 750 (s, $\delta_{CH}$)

$^1$H-NMR (300 MHz, CDCl$_3$, δ [ppm]): 1.47 (d, 3H, $^3$J=7.0 Hz, 5-OCH$_2$CHC$\underline{H}_3$C$_6$H$_5$); 3.34 (sext, 1H, $^3$J=7.0 Hz, 5-OCH$_2$C$\underline{H}$CH$_3$C$_6$H$_5$); 4.45-4.55 (ddd, 2H, $^2$J=9.0 Hz, $^3$J=6.9 Hz, $^3$J=5.4 Hz, 5-OC$\underline{H}_2$CHCH$_3$C$_6$H$_5$); 6.17 (d, 1H, $^3$J=9.8 Hz, 3-H); 6.84 (dd, 1H, $^3$J=2.4 Hz, $^5$J=0.9 Hz, 4'-H); 7.13 (dd, 1H, $^5$J=0.9 Hz; $^5$J=0.7 Hz, 8-H); 7.28-7.39 (m, 5H, 5-OCH$_2$CHCH$_3$C$_6$$\underline{H}_5$); 7.56 (d, 1H, $^3$J=2.4 Hz, 5'-H); 7.82 (dd, 1H, $^3$J=9.8 Hz, $^5$J=0.7 Hz, 4-H)

$^{13}$C-NMR (75.5 MHz, CDCl$_3$, δ [ppm]): 18.03 (5-OCH$_2$CH$\underline{C}$H$_3$C$_6$H$_5$); 40.42 (5-OCH$_2$$\underline{C}$HCH$_3$C$_6$H$_5$); 78.21 (5-O$\underline{C}$H$_2$CHCH$_3$C$_6$H$_5$); 94.17 (8-C); 104.94 (4'-C); 107.02 (4a-C); 112.60 (3-C); 113.68 (6-C); 127.03 (4"-C); 127.37 and 128.75 (2"-C, 3"-C, 5"-C, 6"-C); 139.18 (4-C); 142.91 (1"-C); 144.86 (5'-C); 148.78 (5-C); 152.64 (8a-C); 158.15 (7-C); 161.17 (2-C)

MS (70 eV, m/z, I [% B]): 320 (11, M$^+$); 203 (6); 202 (45, [M-C$_9$H$_{10}$]$^+$); 174 (5, [202-CO]$^+$); 119 (36, [C$_9$H$_{11}$]$^+$); 92 (8); 91 (100, [C$_7$H$_7$]$^+$); 77 (6, [C$_6$H$_5$]$^+$); 51 (6, [C$_4$H$_3$]$^+$); 41 (17)

| C$_{20}$H$_{16}$O$_4$ (320.34): | calculated: | C 74.99% | H 5.03% | O 19.98% |
|---|---|---|---|---|
| | found: | C 74.85% | H 5.03% | O 20.12% |

Example 10 trans-5-(3-Phenyl-2-propenyloxy)psoralen (J 16)

trans-4-(3-Phenyl-2-propenyloxy)-7H-furo[3,2-g][1]benzopyran-7-on 400 mg (2 mmol) of cinnamylbromide were reacted according to the general method. The reaction time was 7 h.

Yield: 104 mg (22%)

Melting point: 140° C.

IR (KBr, [cm$^{-1}$]): 1715 (s, $v_{C=O}$); 1622 and 1606 (s, $v_{C=C}$)

$^1$H-NMR (300 MHz, CDCl$_3$, δ [ppm]): 5.09 (dd, 2H, $^3$J=6.0 Hz, $^4$J=1.2 Hz, 5-OC$\underline{H}_2$(CH)$_2$C$_6$H$_5$); 6.29 (d, 1H, $^3$J=9.8 Hz, 3-H); 6.45 (dt, 1H, $^3$J=15.9 Hz, $^3$J=6.0 Hz, 5-OCH$_2$C$\underline{H}$CHC$_6$H$_5$); 6.76 (d, br, 1H, $^3$J=15.8 Hz, 5-OCH$_2$CHC$\underline{H}$C$_6$H$_5$); 6.98 (dd, 1H, $^3$J=2.4 Hz, $^5$J=0.9 Hz, 4'-H); 7.19 (s, br, 1H, 8-H); 7.29-7.43 (m, 5H, 5-OCH$_2$(CH)$_2$C$_6$$\underline{H}_5$); 7.61 (d, 1H, $^3$J=2.4 Hz, 5'-H); 8.21 (d, 1H, $^3$J=9.8 Hz, 4-H)

$^{13}$C-NMR (75.5 MHz, CDCl$_3$, δ [ppm]): 73.71 (5-O$\underline{C}$H$_2$CHCHC$_6$H$_5$); 94.55 (8-C); 104.90 (4'-C); 107.48 (4a-C); 112.89 (3-C); 114.13 (6-C); 123.36, 128.41 and 134.45 (4"-C and 5-OCH$_2$($\underline{C}$H)$_2$C$_6$H$_5$); 126.70 and 128.75 (2"-C, 3"-C, 5"-C, 6"-C); 135.91 (1"-C); 139.35 (4-C); 145.12 (5'-C); 148.59 (5-C); 152.67 (8a-C); 158.15 (7-C); 161.18 (2-C)

MS (70 eV, m/z, I [% B]): 318 (3, M$^+$); 202 (11, [M-C$_9$H$_8$]$^+$); 174 (7, [202-CO]$^+$); 118 (14); 117 (100, [C$_9$H$_9$]$^+$); 116 (11); 115 (34); 91 (13, [C$_7$H$_7$]$^+$); 89 (8); 63 (8); 51 (11, [C$_4$H$_3$]$^+$)

| C$_{20}$H$_{14}$O$_4$ (318.33): | calculated: | C 75.46% | H 4.43% | O 20.10% |
|---|---|---|---|---|
| | found: | C 74.74% | H 4.44% | O 19.82% |

Example 11

5-Cyclohexylmethoxypsoralen (J 14)

4-Cyclohexylmethoxy-7H-furo[3,2-g][1]benzopyran-7-on 150 mg (0.7 mmol) of bergaptol, 1 ml (7.2 mmol) of cyclohexylmethylbromide, and 0.2 g $K_2CO_3$ in 10 ml of acetone were reacted according to the general method. The reaction time was 23 h.

Yield: 79 mg (36%)

Melting point: 153.5° C.

IR (KBr, [cm$^{-1}$]): 2929 and 2848 (s, $v_{CH}$); 1721 (s, $v_{C=O}$); 1620 and 1603 (s, $v_{C=C}$); 750 (s, $\delta_{CH}$)

$^1$H-NMR (300 MHz, CDCl$_3$, δ [ppm]): 1.13-1.38 and 1.73-1.94 (2x m, 5H and 6H, 5-OCH$_2$C$_6$$\underline{H}$$_{11}$); 4.24 (d, 2H, $^3$J=5.9 Hz, 5-OC$\underline{H}$$_2$C$_6$H$_{11}$); 6.28 (d, 1H, $^3$J=9.8 Hz, 3-H); 6.95 (dd, 1H, $^3$J=2.4 Hz, $^5$J=0.9 Hz, 4'-H); 7.13 (s, br, 1H, 8-H); 7.57 (d, 1H, $^3$J=2.4 Hz, 5'-H); 8.17 (d, 1H, $^3$J=9.8 Hz, 4-H)

$^{13}$C-NMR (75.5 MHz, CDCl$_3$, δ [ppm]): 25.76 (3"-C, 5"-C); 26.41 (4"-C); 29.81 (2"-C, 6"-C); 38.55 (1"-C); 78.33 (5-O$\underline{C}$H$_2$C$_6$H$_{11}$); 93.76 (8-C); 105.27 (4'-C); 106.73 (4a-C); 112.52 (3-C); 113.24 (6-C); 139.37 (4-C); 144.67 (5'-C); 149.31 (5-C); 152.78 (8a-C); 158.34 (7-C); 161.32 (2-C)

MS (70 eV, m/z, I [% B]): 298 (12, M$^+$); 203 (14); 202 (94, [M-C$_7$H$_{12}$]$^+$); 174 (15, [202-CO]$^+$); 97 (12, [C$_7$H$_{13}$]$^+$); 69 (7); 55 (100, [C$_4$H$_7$]$^+$); 51 (6, [C$_4$H$_3$]$^+$); 43 (8); 41 (26)

| $C_{18}H_{18}O_4$ (298.34): | calculated: | C 72.47% | H 6.08% | O 21.45% |
|---|---|---|---|---|
| | found: | C 72.35% | H 5.99% | O 21.66% |

Example 12

5-(2-Cyclohexylethoxy)psoralen (J 23)

4-(2-Cyclohexylethoxy)-7H-furo[3,2-g][1]benzopyran-7-on 0.5 ml (3.3 mmol) of 2-cyclohexylethylbromide were reacted according to the general method. The reaction time was 24 h.

Yield: 263 mg (57%)

Melting point: 117° C.

IR (KBr, [cm$^{-1}$]): 2919 and 2845 (s, $v_{CH}$); 1723 (s, $v_{C=O}$); 1625 and 1603 (s, $v_{C=C}$); 748 (m, $\delta_{CH}$)

$^1$H-NMR (300 MHz, CDCl$_3$, δ [ppm]): 0.95-1.81 (m, 13H, 5-OCH$_2$C$\underline{H}$$_2$C$_6$$\underline{H}$$_{11}$); 4.49 (t, 2H, $^3$J=6.6 Hz, 5-OC$\underline{H}$$_2$CH$_2$C$_6$H$_5$); 6.28 (d, 1H, $^3$J=9.8 Hz, 3-H); 6.95 (dd, 1H, $^3$J=2.4 Hz, $^5$J=1.0 Hz, 4'-H); 7.13 (s, br, 1H, 8-H); 7.58 (d, 1H, $^3$J=2.4 Hz, 5'-H); 8.15 (dd, 1H, $^3$J=9.8 Hz, $^5$J=0.5 Hz, 4-H)

$^{13}$C-NMR (75.5 MHz, CDCl$_3$, δ [ppm]): 26.21 (3"-C, 5"-C); 26.43 (4"-C); 33.31 (2"-C, 6"-C); 34.60 (1"-C); 37.35 (5-OCH$_2$$\underline{C}$H$_2$C$_6$H$_{11}$); 71.07 (5-O$\underline{C}$H$_2$CH$_2$C$_6$H$_{11}$); 93.79 (8-C); 105.24 (4'-C); 106.79 (4a-C); 112.52 (3-C); 113.23 (6-C); 139.42 (4-C); 144.71 (5'-C); 149.16 (5-C); 152.77 (8a-C); 158.33 (7-C); 161.30 (2-C)

MS (70 eV, m/z, I [% B]): 312 (13, M$^+$); 203 (18); 202 (98, [M-C$_8$H$_{14}$]$^+$); 174 (13, [202-CO]$^+$); 111 (12, [C$_8$H$_{15}$]$^+$); 69 (100); 67 (10); 55 (71, [C$_4$H$_7$]$^+$); 43 (9); 41 (54)

| $C_{19}H_{20}O_4$ (312.36): | calculated: | C 73.06% | H 6.45% | O 20.49% |
|---|---|---|---|---|
| | found: | C 73.11% | H 6.52% | O 20.37% |

Example 13

5-(3-Cyclohexylpropoxy)psoralen (J 21)

4-(3-Cyclohexylpropoxy)-7H-furo[3,2-g][1]benzopyran-7-on 0.9 ml (5.4 mmol) of 3-cyclohexylpropylchloride were reacted according to the general method. The reaction time was 38 h.

Yield: 223 mg (46%)

Melting point: 115° C.

IR (KBr, [cm$^{-1}$]): 2921 and 2849 (s, $v_{CH}$); 1720 (s, $v_{C=O}$); 1618 and 1604 (m, $v_{C=C}$); 754 (m, $\delta_{CH}$)

$^1$H-NMR (300 MHz, CDCl$_3$, δ [ppm]): 0.87-1.93 (m, 15H, 5-OCH$_2$(CH$_2$)$_2$C$_6$H$_{11}$); 4.43 (t, 2H, $^3$J=6.5 Hz, 5-OCH$_2$(CH$_2$)$_2$C$_6$H$_{11}$); 6.28 (d, 1H, $^3$J=9.8 Hz, 3-H); 6.94 (dd, 1H, $^3$J=2.4 Hz, $^5$J=1.0 Hz, 4'-H); 7.13 (t, 1H, $^5$J=0.8 Hz, 8-H); 7.58 (d, 1H, $^3$J=2.4 Hz, 5'-H); 8.18 (dd, 1H, $^3$J=9.8 Hz, $^5$J=0.6 Hz, 4-H)

$^{13}$C-NMR (75.5 MHz, CDCl$_3$, δ [ppm]): 26.33 (3"-C, 5"-C), 26.60, 27.44 and 33.66 (4"-C and 5-OCH$_2$(CH$_2$)$_2$C$_6$H$_{11}$); 33.36 (2"-C, 6"-C); 37.47 (1"-C); 73.42 (5-OCH$_2$(CH$_2$)$_2$C$_6$H$_{11}$); 93.83 (8-C); 105.19 (4'-C); 106.82 (4a-C); 112.53 (3-C); 113.31 (6-C); 139.41 (4-C); 144.73 (5'-C); 149.15 (5-C); 152.76 (8a-C); 158.31 (7-C); 161.31 (2-C)

MS (70 eV, m/z, I [% B]): 326 (19, M$^+$); 203 (17); 202 (100, [M-C$_9$H$_{16}$]$^+$); 174 (15, [202-CO]$^+$); 83 (30); 69 (57); 57 (11); 55 (71, [C$_4$H$_7$]$^+$); 43 (11); 41 (63)

| C$_{20}$H$_{22}$O$_4$ (326.39): | calculated: | C 73.60% | H 6.79% | O 19.61% |
|---|---|---|---|---|
| | found: | C 73.64% | H 6.86% | O 19.50% |

Example 14

Inhibition of Lymphocyte Proliferation by J19 (=Psora-4)

[$^3$H]-Thymidine incorporation assay: Human peripheral blood mononuclear cells (PBMC) were seeded at 2×10$^5$ cells per well in RPMI culture medium in flat-bottom 96 well plates (final volume 200 µl), pre-incubated with increasing concentrations of Psora-4 for 30 min and then stimulated with 200 ng/ml soluble anti-CD3 mAb (Biomeda) for 48 hr. MBP-specific CD4$^+$ human memory T cells at 5×10$^4$ cells per well were stimulated with 200 ng/ml anti-CD3 mAb in the presence of 5×10$^4$ autologous irradiated PBMCs (2500 rad). PAS T cells (2×10$^4$ cells per well) were stimulated in the presence of 2×10$^6$ irradiated Lewis rat thymocytes (2500 rad) as antigen presenting cells with 10 µg/ml MBP. [$^3$H]-TdR (1 µCi per well) was added for the last 16 hr. Cells were harvested onto glass fiber filters and radioactivity measured in a beta-scintillation counter.

Figure 1:
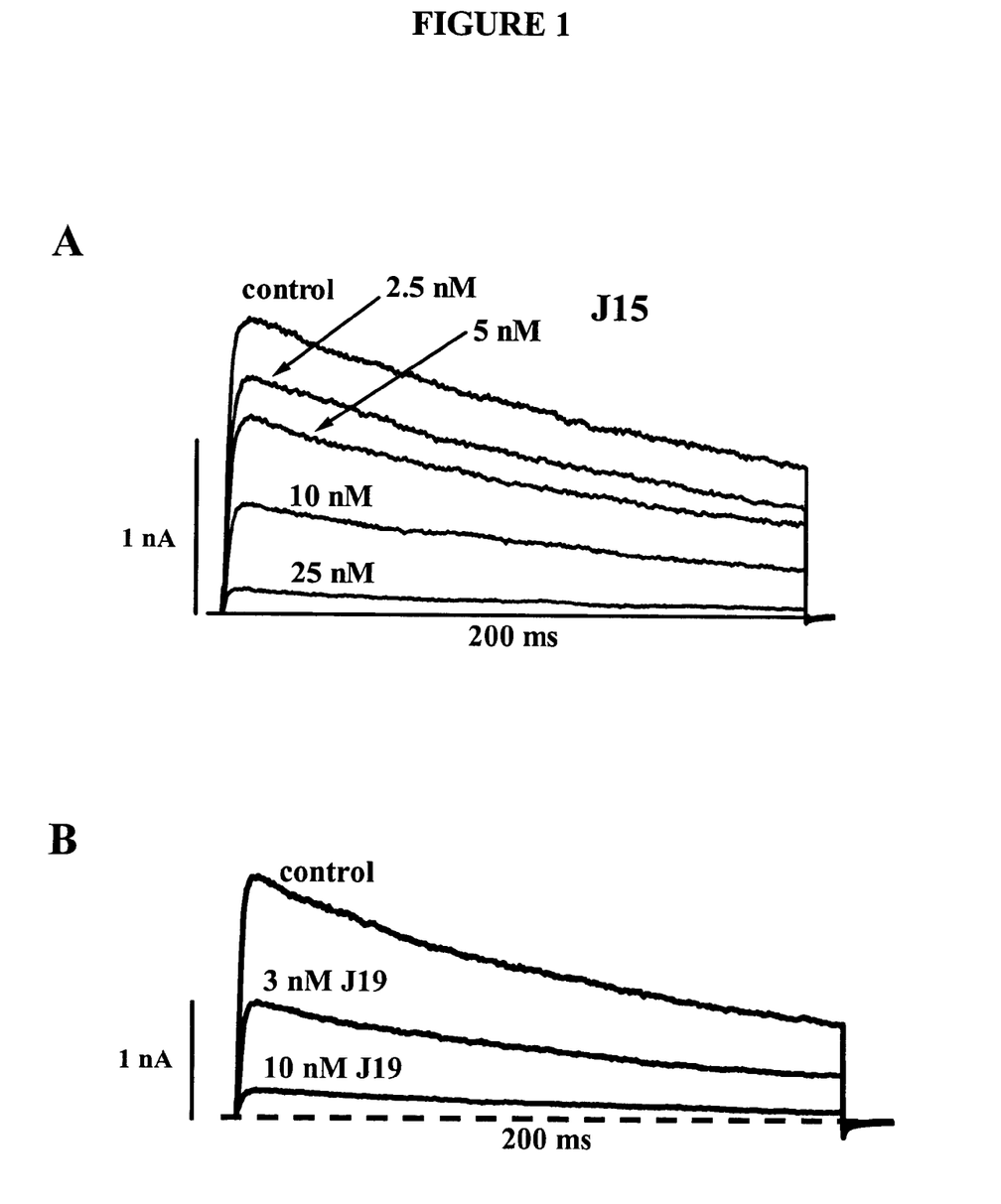
FIG. 1A shows dose-dependent inhibition of Kv1.3 current by compound J15.
FIG. 1B shows dose-dependent inhibition of Kv1.3 current by compound J19.
Figure 2:
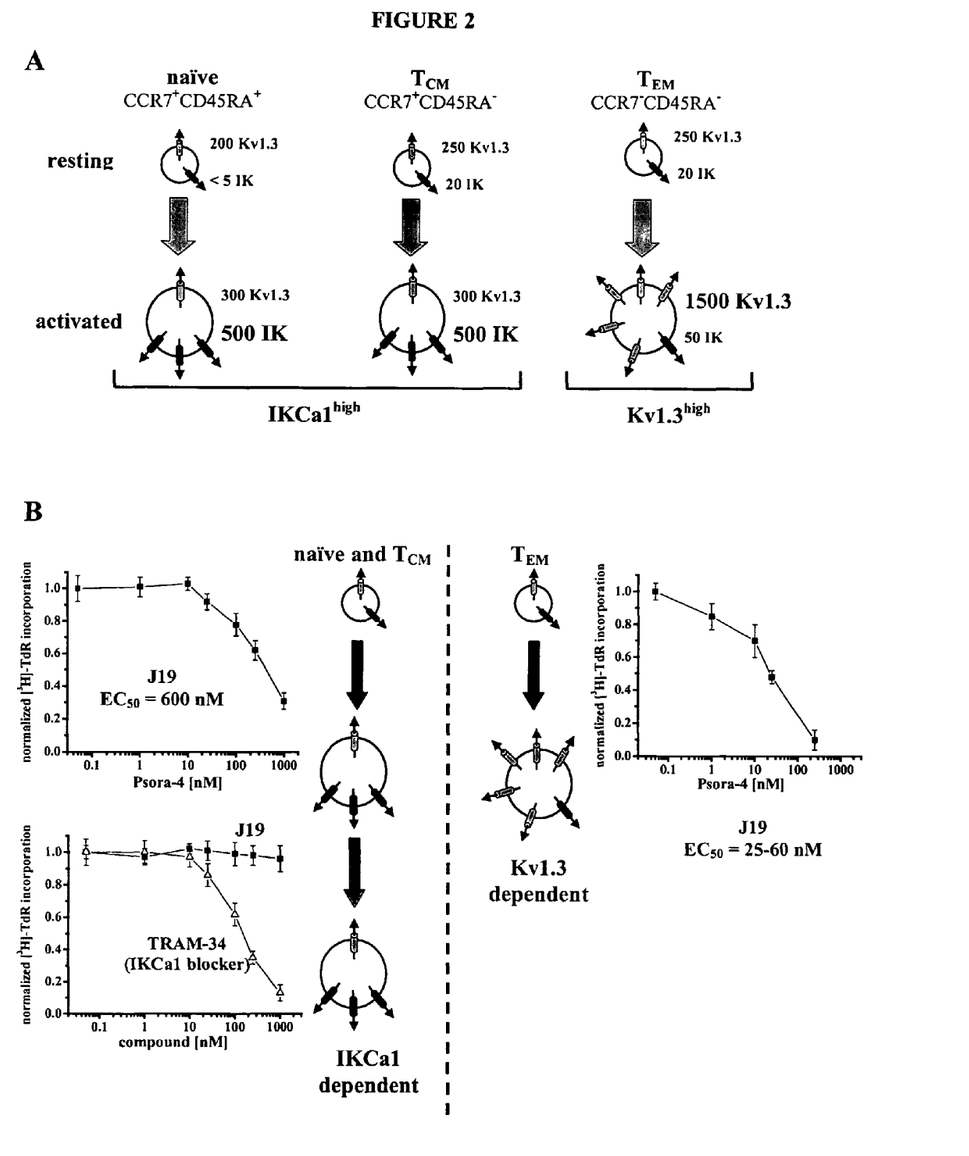
FIG. 2A shows a cartoon of Kv1.3 and IKCa1 expression in naïve, $T_{CM}$ and $T_{EM}$ cells in the resting and in the activated state.
FIG. 2B shows the effect of J19 on the proliferation of naïve and $T_{CM}$ T cells (left) versus $T_{EM}$ cells (right). Note the difference in potency.

Results are shown in 2B.

Human MBP-specific CD4$^+$ memory T cells were generated from PBMCs from a healthy volunteer with the help of the split well assay. Cells were stimulated 12× with MBP and used for the proliferation assay when they were >95% CCR7$^-$ CD45RA$^-$ by flow cytometry.

Block of Kv1.3, selectivity over sodium channels (S) and LogP values of 5-Phenylalkoxy- and 5-Cyclohexylalkoxypsoralens Electrophysiology. All experiments were conducted in the whole-cell configuration of the patch-clamp technique with a holding potential of −80 mV on a cell line stably expressing Kv1.3. Pipette resistances averaged 2.0 MΩ, and series resistance compensation of 80% was employed when currents exceeded 2 nA. Kv1.3 currents were elicited by repeated 200 ms or 2 sec pulses from −80 mV to 40 mV, applied at intervals of 30 or 60 s. Kv1.3 currents were recorded in normal Ringer solution with a calcium-free pipette solution containing (in mM): 145 KF, 10 HEPES, 10 EGTA, 2 MgCl$_2$, pH 7.2, 300 mOsm.

| compound | $K_d$ Kv1.3 | S | LogP |
|---|---|---|---|
| 5-MOP | 100 µM | 14 | 2.15 |
| 5-BOP | 350 ± 72 nM | 43 | 3.25 |
| J 09 | 169 ± 16 nM | 41 | 3.55 |
| J 15 | 6.3 ± 1.0 nM | 397 | 3.97 |
| J 19 (Psora 4) | 2.9 ± 0.3 nM | 483 | 4.33 |
| J 22 | 6.1 ± 0.7 nM | 262 | 4.71 |
| J 16 | 172 ± 37 nM | 41 | 3.79 |
| J 12 | 72 ± 12 nM | 25 | 3.87 |
| J 17 | 68 ± 12 nM | 38 | 4.12 |
| J 20 | 3.5 ± 0.5 nM | 286 | 4.40 |
| J 14 | 138 ± 17 nM | 48 | 4.41 |
| J 23 | 132 ± 33 nM | 11 | 4.82 |
| J 21 | 144 ± 43 nM | 8 | 5.34 |

Table showing the $K_d$s (mean ± S.D.), the selectivity (S) over Na$_v$1.2 and the logP values of the synthesized compounds. S = $K_d$ Nav1.2/$K_d$ Kv1.3. LogP values were determined by HPLC.

Selectivity of J 19 (Psora-4) Over Other Potassium Channels

| J 19 (Psora 4) | $K_d$ [nM] |
|---|---|
| Kv1.1 | 62 ± 9 |
| Kv1.2 | 49 ± 6 |
| Kv1.3 (cloned) | 2.9 ± 0.3 |
| Kv1.3 (human T) | 3.0 ± 0.3 |
| Kv1.4 | 202 ± 12 |
| Kv1.5 | 7.7 ± 0.9 |
| Kv1.7 | 100 ± 12 |
| Kv3.1 | >1000 |
| HERG | >1000 |
| IKCa1 | >1000 |
| SKCa3 | >1000 |
| BK | >1000 |
| Nav1.2 (N1E-115) | >1000 |

Affinity of Psora-4 to cloned and native ion channels. Psora-4 was tested at three to five concentrations (n = 3). All values were determined by whole-cell patch-clamp.

The compounds described herein may be administered by routes of administrations known to one skilled in the art and may be formulated as tablets, solutions, suspensions, gels, creams, ointments, patches and the like.

While this invention has been described with respect to various specific examples and embodiments, it is to be understood that the invention is not limited thereto and that it can be variously practiced with the scope of the following claims.

What is claimed is:

1. A method for causing immunosuppression or treating an autoimmune disorder in a human or veterinary patient, said method comprising the step of:
    administering to the patient, in an amount that is effective to cause therapeutic inhibition of Kv1.3 potassium channels in T lymphocytes of the patient, a 5-phenylalkoxypsoralen compound having the structure:

wherein;
R1 is an aromatic group and
X is a functionalized or unfunctionalized cyclic hydrocarbyl group that comprises from 3 to 5 carbon atoms or an acyclic hydrocarbyl group having from 2 to 5 carbon atoms.

2. A method according to claim 1 wherein the compound is a 5-phenylalkoxypsoralen.

3. A method according to claim 1 wherein the compound is a 5-cyclohexylalkoxypsoralen.

4. A method according to claim 1 wherein the compound is 5-(2-Phenylethoxy)psoralen.

5. A method according to claim 1 wherein the compound is 5-(3-Phenylpropoxy)psoralen.

6. A method according to claim 1 wherein the compound is 5-(4-Phenylbutoxy)psoralen.

7. A method according to claim 1 wherein the compound is 5-(5-Phenylpentoxy)psoralen.

8. A method according to claim 1 wherein the compound is 5-Biphenylmethoxypsoralen.

9. A method according to claim 1 wherein the compound is 5-Diphenylmethoxypsoralen.

10. A method according to claim 1 wherein the compound is R,S-5-(2-Phenylpropoxy)psoralen.

11. A method according to claim 1 wherein the compound is trans-5-(3-Phenyl-2-propenyloxy)psoralen.

12. A method according to claim 1 wherein the method is carried out to treat rheumatoid arthritis.

13. A method according to claim 1 wherein the method is carried out to treat multiple sclerosis.

14. A method according to claim 1 wherein the method is carried out to prevent graft rejection.

* * * * *